United States Patent
Yaguchi et al.

(10) Patent No.: US 11,227,391 B2
(45) Date of Patent: *Jan. 18, 2022

(54) IMAGE PROCESSING APPARATUS, MEDICAL IMAGE DIAGNOSTIC APPARATUS, AND PROGRAM

(71) Applicant: Canon Medical Systems Corporation, Otawara (JP)

(72) Inventors: Atsushi Yaguchi, Tokyo (JP); Tomoya Okazaki, Hachioji (JP); Yasunori Taguchi, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/116,347

(22) Filed: Dec. 9, 2020

(65) Prior Publication Data

US 2021/0104044 A1    Apr. 8, 2021

Related U.S. Application Data

(63) Continuation of application No. 16/023,864, filed on Jun. 29, 2018, now Pat. No. 10,896,504.

(30) Foreign Application Priority Data

Jun. 30, 2017    (JP) .............................. JP2017-129423

(51) Int. Cl.
*G06T 7/00*    (2017.01)
*G06T 7/44*    (2017.01)
(Continued)

(52) U.S. Cl.
CPC .......... *G06T 7/0014* (2013.01); *G06K 9/4642* (2013.01); *G06K 9/4647* (2013.01);
(Continued)

(58) Field of Classification Search
CPC ........................... G06T 7/0014; G06K 9/4642
See application file for complete search history.

(56) References Cited

U.S. PATENT DOCUMENTS

| 7,236,619 B2 * | 6/2007 | Doi | G06T 7/0012 382/128 |
|---|---|---|---|
| 2014/0037170 A1 | 2/2014 | Sekiguchi et al. | |
| 2016/0217572 A1 * | 7/2016 | Akahori | A61B 5/0044 |

FOREIGN PATENT DOCUMENTS

| JP | 2014-30623 A | 2/2014 |
|---|---|---|
| JP | 2015-73832 A | 4/2015 |

OTHER PUBLICATIONS

D. M. Hansell, et al., "Fleischner Society: Glossary of Terms for Thoracic Imaging", Radiology, vol. 246, No. 3, Mar. 2008, pp. 26.

(Continued)

*Primary Examiner* — Tuan H Nguyen
(74) *Attorney, Agent, or Firm* — Oblon, McClelland, Maier & Neustadt, L.L.P.

(57) ABSTRACT

According to one embodiment, an image processing apparatus includes processing circuitry. The processing circuitry is configured to acquire medical image data. The processing circuitry is configured to obtain spatial distribution of likelihood values representing a likelihood of corresponding to a textual pattern in a predetermined region of a medical image for each of a plurality of textual patterns based on the medical image data. The processing circuitry is configured to calculate feature values in the predetermined region of the medical image based on the spatial distribution obtained for the each of the plurality of textual patterns.

16 Claims, 12 Drawing Sheets

(51) Int. Cl.
*G06T 11/00* (2006.01)
*G06K 9/46* (2006.01)
*G16H 30/20* (2018.01)
*G16H 50/20* (2018.01)
*G06T 7/45* (2017.01)
*G06T 7/41* (2017.01)
*G06K 9/56* (2006.01)
*G06K 9/62* (2006.01)
*G16H 30/40* (2018.01)

(52) U.S. Cl.
CPC .............. *G06K 9/56* (2013.01); *G06K 9/6277* (2013.01); *G06T 7/0012* (2013.01); *G06T 7/41* (2017.01); *G06T 7/44* (2017.01); *G06T 7/45* (2017.01); *G06T 11/005* (2013.01); *G16H 30/20* (2018.01); *G16H 30/40* (2018.01); *G16H 50/20* (2018.01); *G06K 2209/05* (2013.01); *G06T 2207/10081* (2013.01); *G06T 2207/10088* (2013.01); *G06T 2207/10104* (2013.01); *G06T 2207/10108* (2013.01); *G06T 2207/20072* (2013.01); *G06T 2207/20081* (2013.01); *G06T 2207/20084* (2013.01); *G06T 2207/30061* (2013.01); *G06T 2207/30096* (2013.01); *G06T 2207/30101* (2013.01)

(56) References Cited

OTHER PUBLICATIONS

V. Lepetit, et al., "Keypoint Recognition Using Randomized Trees", IEEE Transactions of Pattern Analysis and Machine Intelligence, vol. 28, Issue. 9, Sep. 2006, pp. 15.

A. F. Frangi, et al., "Multiscale vessel enhancement filtering". MICCI (Medical Image Computing and Computer-Assisted), vol. 1496, 1998, , pp. 6.

Japanese Office Action dated Feb. 16, 2021 in Japanese Patent Application No. 2017-129423, citing documents AO and AP therein, 3 pages.

* cited by examiner

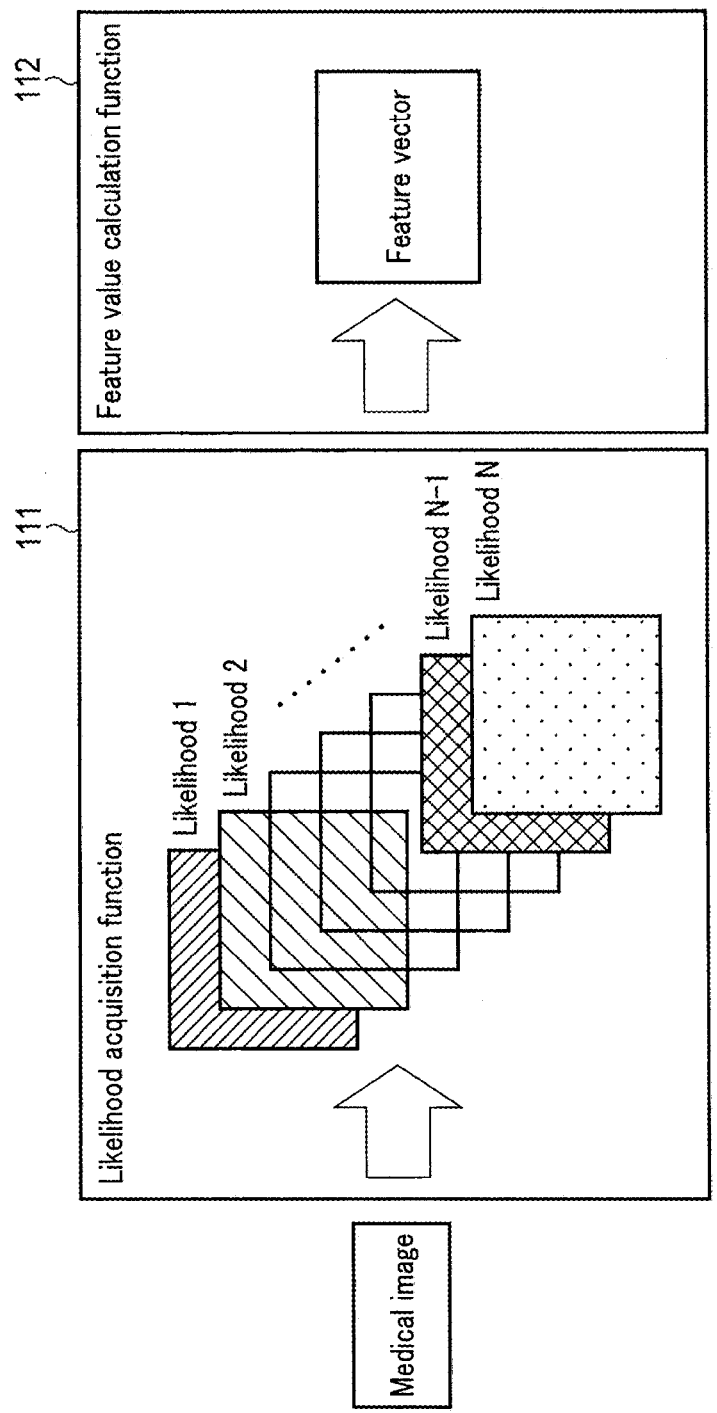
F I G. 3

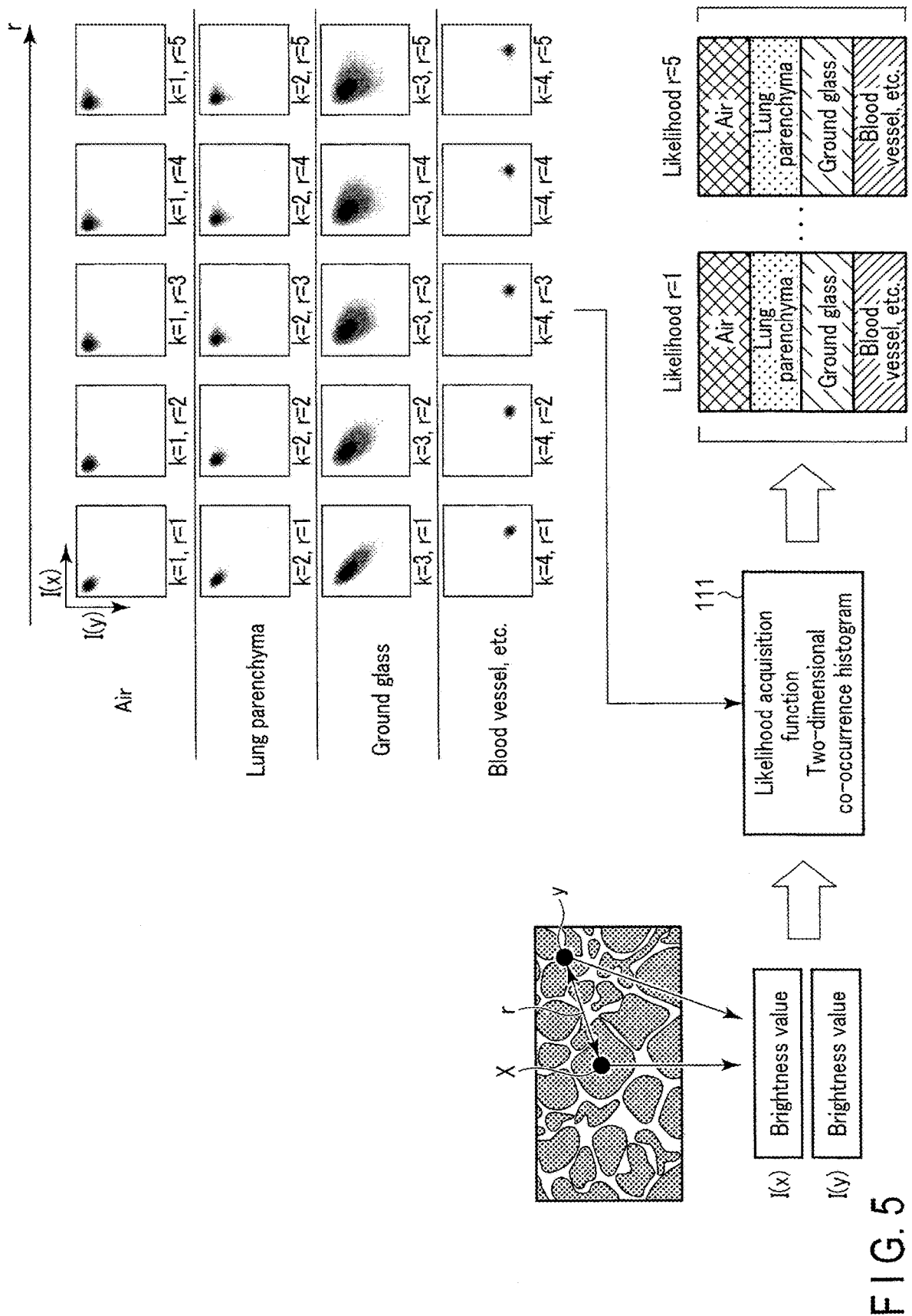
F I G. 5

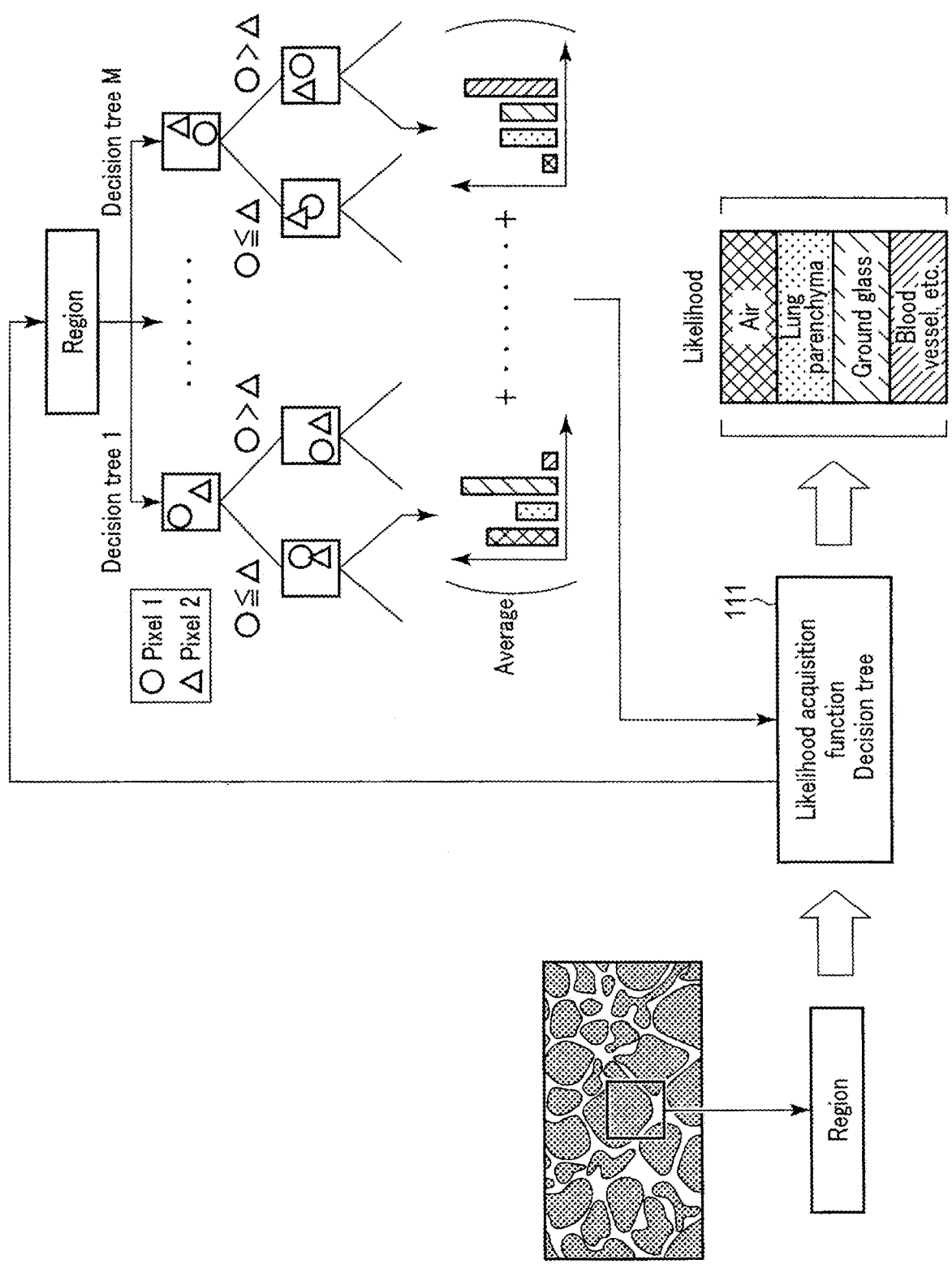
F I G. 7

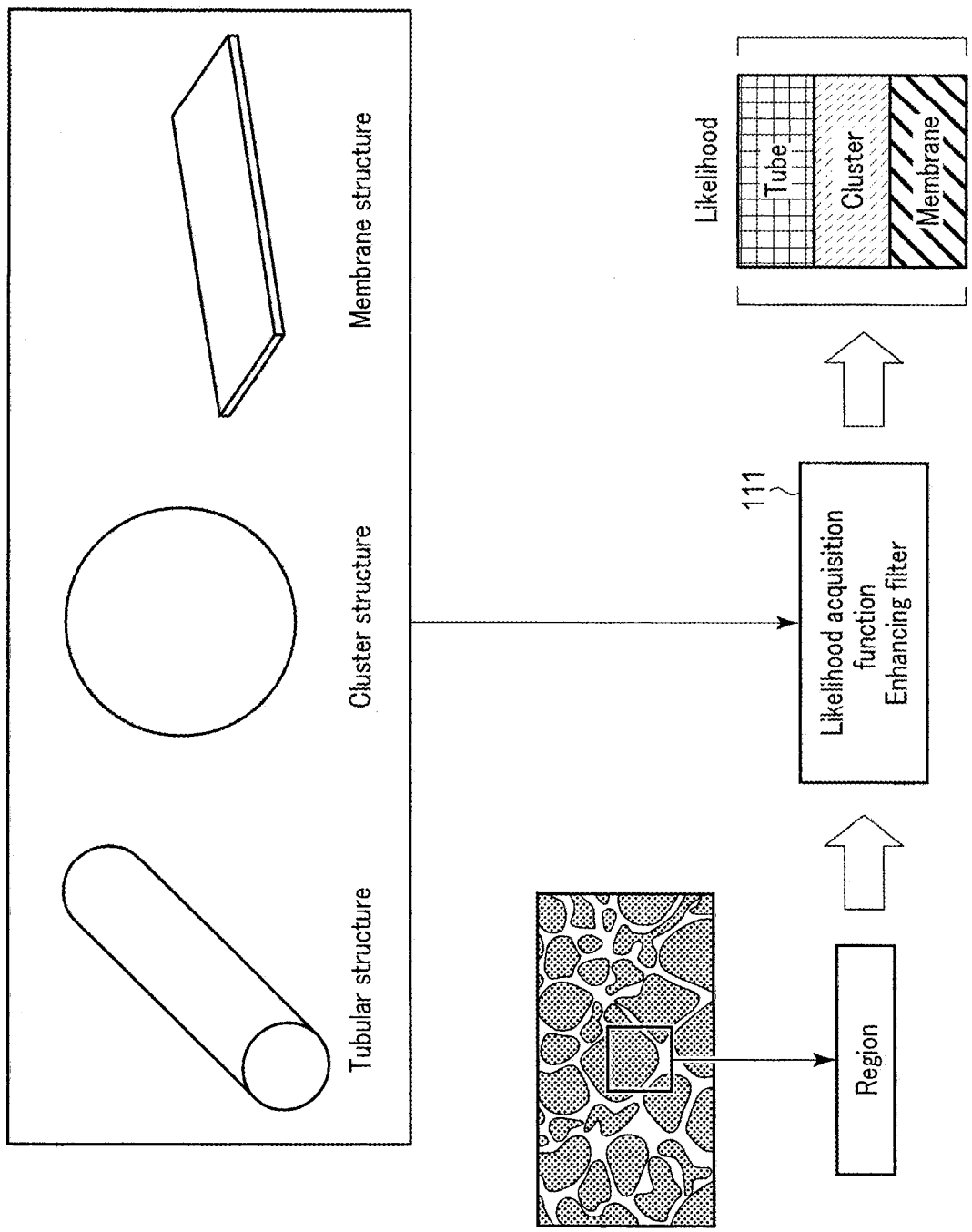
F I G. 8

IMAGE PROCESSING APPARATUS, MEDICAL IMAGE DIAGNOSTIC APPARATUS, AND PROGRAM

CROSS-REFERENCE TO RELATED APPLICATIONS

This application is a continuation of U.S. Application Ser. No. 16/023,864, filed Jun. 29, 2018, which is based upon and claims the benefit of priority from the prior Japanese Patent Application No. 2017-129423, filed Jun. 30, 2017, the entire contents of each of the above-identified documents are incorporated herein by reference.

FIELD

Embodiments described herein relate generally to an image processing apparatus, a medical image diagnostic apparatus, and a program.

BACKGROUND

A technique of automatically identifying a textual pattern of an image collected by a medical image diagnostic apparatus, such as an X-ray CT (Computed Tomography) apparatus, is known. This kind of technique is useful for diagnosing diseases, such as diffuse lung disease, which show a characteristic textual pattern on a CT image. Accordingly, this kind of technique is expected to be applied to diagnosis of a predetermined disease, etc.

A doctor performs image interpretation by extracting a characteristic textual pattern from a CT image of a patient. With the increasing high definition of a recent X-ray CT apparatus, etc., detailed image interpretation of a lesion has been possible, but image interpretation with the naked eye is a significant burden on the doctor. In addition, since experience is required for extracting characteristic textual patterns, diagnostic results may vary depending on the doctor.

To solve such a problem, computer-aided diagnosis is recently receiving attention. For example, a method for extracting feature values from a region of interest belonging to a lung field of a CT image and automatically identifying a textual pattern by a trained model of machine learning based on the extracted feature values is known. To improve identification accuracy, design of a feature extraction method is important. Conventionally, however, since feature values are directly extracted from a CT image, it is difficult to extract feature values that are effective for Identification, and thus it may be difficult to improve identification accuracy.

BRIEF DESCRIPTION OF THE DRAWINGS

FIG. 3 is a diagram explaining an operation of processing circuitry shown in FIG. 2.

FIG. 5 is a diagram showing another example of the processing in which a likelihood value is acquired by the likelihood acquisition function shown in FIG. 2.

FIG. 7 is a diagram showing an example of processing in which a likelihood value is acquired by a decision tree model by the likelihood acquisition function shown in FIG. 2.

FIG. 8 is a diagram showing an example of processing in which a likelihood value relating to a structure is acquired by a structure enhancing filter by the likelihood acquisition function shown in FIG. 2.

DETAILED DESCRIPTION

In general, according to one embodiment, an image processing apparatus includes processing circuitry. The processing circuitry is configured to acquire medical image data. The processing circuitry is configured to obtain spatial distribution of likelihood values representing a likelihood of corresponding to a textual pattern in a predetermined region of a medical image for each of a plurality of textual patterns based on the medical image data. The processing circuitry is configured to calculate feature values in the predetermined region of the medical image based on the spatial distribution obtained for the each of the plurality of textual patterns.

Embodiments will be described with reference to the drawings.

Figure 1:
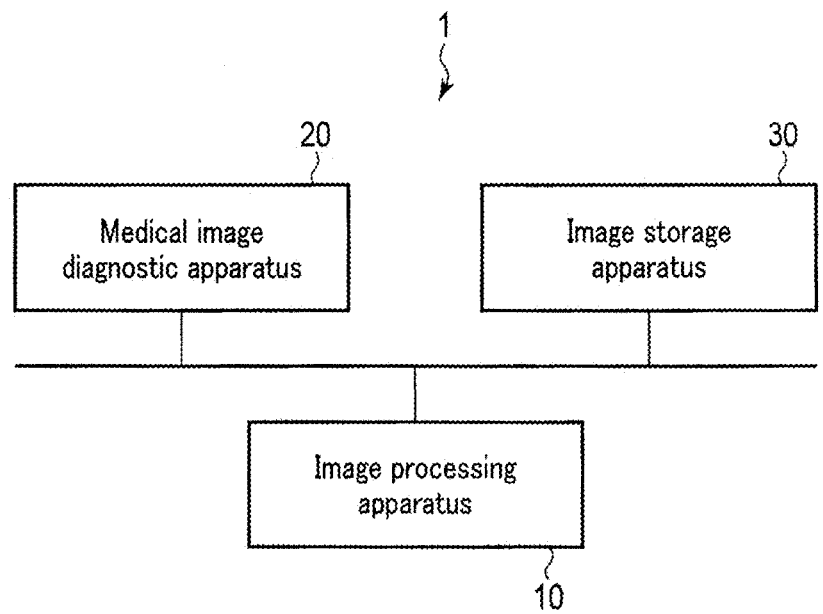
FIG. 1 is a diagram showing a medical information system including an image processing apparatus according to a present embodiment.

FIG. 1 is a diagram showing an example of a medical information system 1 including an image processing apparatus 10 according to a present embodiment. The medical information system 1 shown in FIG. 1 comprises the image processing apparatus 10, a medical image diagnostic apparatus 20, and an image storage apparatus 30. The image processing apparatus 10, the medical image diagnostic apparatus 20, and the image storage apparatus 30 are, for example, directly or indirectly connected by an intra-hospital Local Area Network (LAN) installed in a hospital to be able to communicate with one another. For example, in a case where the image storage apparatus 30 constitutes a Picture Archiving and Communication System (PACS), the image processing apparatus 10, the medical image diagnostic apparatus 20, and the image storage apparatus 30, for example, mutually transmit and receive medical image data in conformity with a Digital Imaging and Communications in Medicine (DICOM) standard.

The medical image diagnostic apparatus 20 is an apparatus for generating medical image data by photographing a subject. The medical image diagnostic apparatus 20 is, for example, an X-ray diagnostic apparatus, an X-ray Computed Tomography (CT) apparatus, a Magnetic Resonance Imaging (MR) apparatus, an ultrasonic diagnostic apparatus, a Single Photon Emission Computed Tomography (SPECT) apparatus, a Positron Emission computed Tomography (PET) apparatus, a SPECT-CT apparatus having a SPECT apparatus and an X-ray CT apparatus integrated as one unit, a PET-CT apparatus having a PET apparatus and an X-ray CT apparatus integrated as one unit, a PET-MRI apparatus having a PET apparatus and an MRI apparatus integrated as one unit, or an apparatus group thereof.

The image storage apparatus 30 is a database storing medical image data. The image storage apparatus 30, for example, stores, in a memory provided inside thereof, medical image data generated in the image processing apparatus 10 and the medical image diagnostic apparatus 20.

Figure 2:
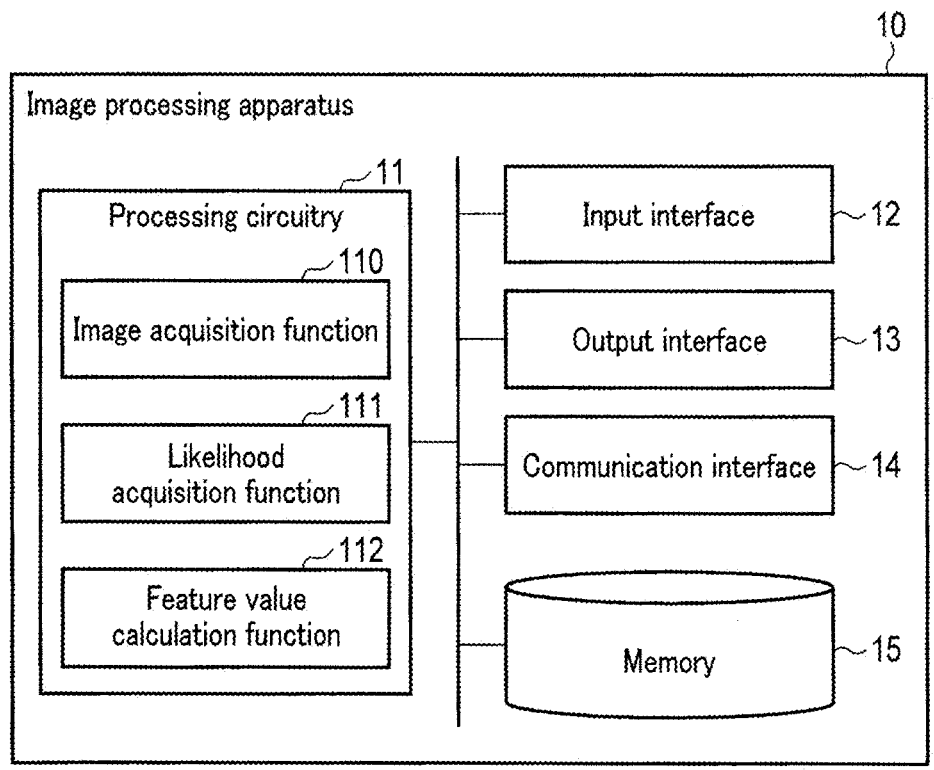
FIG. 2 is a diagram showing a functional configuration of the image processing apparatus shown in FIG. 1.

The image processing apparatus 10 is an apparatus for performing image processing for the medical image data generated in the medical image diagnostic apparatus 20 and medical image data read from the image storage apparatus 30. FIG. 2 is a diagram showing an example of a functional configuration of the image processing apparatus 10 according to the present embodiment. The image processing apparatus 10 shown in FIG. 2 has processing circuitry 11, an input interface 12, an output interface 13, a communication interface 14, and a memory 15.

The processing circuitry 11 is a processor that functions as a main unit of the image processing apparatus 10. The processing circuitry 11 executes a program stored in the memory 15 to realize a function corresponding to the executed program. Note that the processing circuitry 11 may comprise a storage area storing at least a part of data stored in the memory IS.

The input interface 12 accepts various operations that are input to the image processing apparatus 10 by an operator. The input interface 12 is realized by, for example, a mouse, a keyboard, or a touch panel into which an instruction is input with a touch on an operation surface. The input interface 12 is connected to the processing circuitry 11, converts an operation instruction input by an operator into an electric signal, and outputs the electric signal to the processing circuitry 11. In the present specification, the input interface 12 is not limited to an interface including physical operation components, such as a mouse, a keyboard, etc. For example, processing circuitry of electric signals, which receives an electric signal corresponding to an operation instruction input from an external input device provided separately from the image processing apparatus 10 and outputs this electric signal to the processing circuitry 11, is also included in examples of the input interface 12.

The output interface 13 is connected to the processing circuitry 11, and outputs a signal supplied from the processing circuitry 11. The output interface 13 is, for example, display circuitry, and is realized by, for example, a CRT display, a liquid crystal display, an organic EL display, an LED display, and a plasma display. The display circuitry, for example, displays a medical image based on medical image data. Note that processing circuitry, which converts data representing a display target into a video signal and outputs the video signal to the outside, is also included in the output interface 13.

The communication interface 14 is, for example, connected to an intra-hospital network. The communication interface 14, for example, receives medical image data from the medical image diagnostic apparatus 20 and the image storage apparatus 30 via the intra-hospital network.

The memory 15 includes a processor-readable storage medium, etc., such as a magnetic or optical storage medium, or a semiconductor memory. The memory 15 may be a driving device, etc., which reads and writes various types of information relative to a portable storage medium, such as a CD-ROM drive, a DVD drive, and a flash memory. Note that the memory 15 does not necessarily need to be realized by a single storage device. For example, the memory 15 may be realized by a plurality of storage devices.

The memory 15 stores received data in accordance with control from the processing circuitry 11. For example, the memory 15 stores medical image data output from the medical image diagnostic apparatus 20 and the image storage apparatus 30.

In addition, the memory 15 reads stored data in accordance with control from the processing circuitry 11. For example, the memory 15 reads stored medical image data in accordance with control from the processing circuitry 11. In addition, for example, the memory 15 stores a program according to the present embodiment. The memory 15 reads a stored program in accordance with control from the processing circuitry 11. In addition, the memory 15, for example, stores data relating to frequency distributions of substances and structures in a body, data relating to decision tree model, data relating to a structure enhancing filter, and data relating to a weighting factor. The memory 15 reads stored various data in accordance with control from the processing circuitry 11.

The processing circuitry 11 according to the present embodiment executes a program according to the present embodiment to calculate a feature value using a likelihood that an element included in a medical image is likely to be classified into a classification item corresponding to a predetermined feature. Specifically, the processing circuitry 11 has an image acquisition function 110, a likelihood acquisition function 111, and a feature value calculation function 112 by executing a program stored in the memory 15.

The image acquisition function 110 is a function to acquire desired medical image data. For example, when executing the image acquisition function 110, the processing circuitry 11 reads medical image data stored in the memory 15. Note that the image acquisition function 110 may acquire desired medical image data from the medical image diagnostic apparatus 20 and the image storage apparatus 30.

The likelihood acquisition function 111 is a function to acquire a likelihood representing the likelihood that an element included in a medical image is classified into a classification item corresponding to a predetermined configuration. For example, when executing the likelihood acquisition function 111, the processing circuitry 11 generates an image of multiple channels by acquiring N types of likelihood values for each pixel in a medical image. FIG. 3 is a diagram schematically explaining an operation of the processing circuitry 11 according to the present embodiment. According to FIG. 3, the processing circuitry 11 generates likelihood images of likelihood 1 to likelihood N by acquiring likelihood values for each pixel of a medical image.

The feature value calculation function 112 is a function to calculate a feature value based on the likelihood values acquired by the likelihood acquisition function 111. For example, when executing the feature value calculation function 112, the processing circuitry 11 calculates a plurality of feature values using a plurality of acquired likelihood values, and generates a feature vector from the plurality of calculated feature values. According to FIG. 3, the processing circuitry 11 generates a feature vector based on the likelihood images of likelihood 1 to likelihood N.

Next, processing of the likelihood acquisition function 111 shown in FIG. 2 will be specifically described. In the following, an example will be explained, in which the medical image diagnostic apparatus 20 is an X-ray CT apparatus generating CT image data, and the image processing apparatus 10 receives CT image data generated by the medical image diagnostic apparatus 20 as medical image data.

First, the medical image diagnostic apparatus 20, which is an X-ray CT apparatus, images an imaging region of a subject with X-rays. Specifically, the medical image diagnostic apparatus 20 generates the X-rays from an X-ray tube while rotating a rotation frame to which the X-ray tube and an X-ray detector are attached. The X-ray detector detects the X-rays generated from the X-ray tube and transmitted through the subject. The medical image diagnostic apparatus 20 collects raw data according to the X-rays detected by the X-ray detector by a data acquisition system (DAS), and reconstructs CT image data by an image reconstruction apparatus based on the collected raw data.

The CT image data according to the present embodiment, is assumed to be data representing a slice image showing two-dimensional spatial distribution of a CT value. The slice image consists of a plurality of pixels arranged two-dimensionally. A CT value is allocated to each pixel. In addition, a CT image based on CT image data may be an image of imaging an entire target organ, and may be an image limited to a local region of interest. Note that the CT image data may be data representing a volume image showing three-dimensional spatial distribution of a CT value. The volume image consists of a plurality of voxels arranged three-dimensionally. A CT value is allocated to each voxel.

The medical image diagnostic apparatus 20 transmits generated CT image data to the image processing apparatus 10 via an intra-hospital network. When receiving the CT image data transmitted from the medical image diagnostic apparatus 20, the image processing apparatus 10 stores the received CT image data in the memory 15.

The processing circuitry 11 of the image processing apparatus 10, for example, executes the image acquisition function 110 when an instruction to start image processing is input from an operator through the input interface 12. When executing the image acquisition function 110, the processing circuitry 11 reads CT image data desired by the operator from the memory 15. When the CT image data is read, the processing circuitry 11 executes the likelihood acquisition function 111. When the likelihood acquisition function 111 is executed, based on pixel values (brightness values) of pixels included in the CT image data, the processing circuitry 11 acquires a likelihood value for each of substances and structures in a body, which are represented by the pixels.

Figure 4:
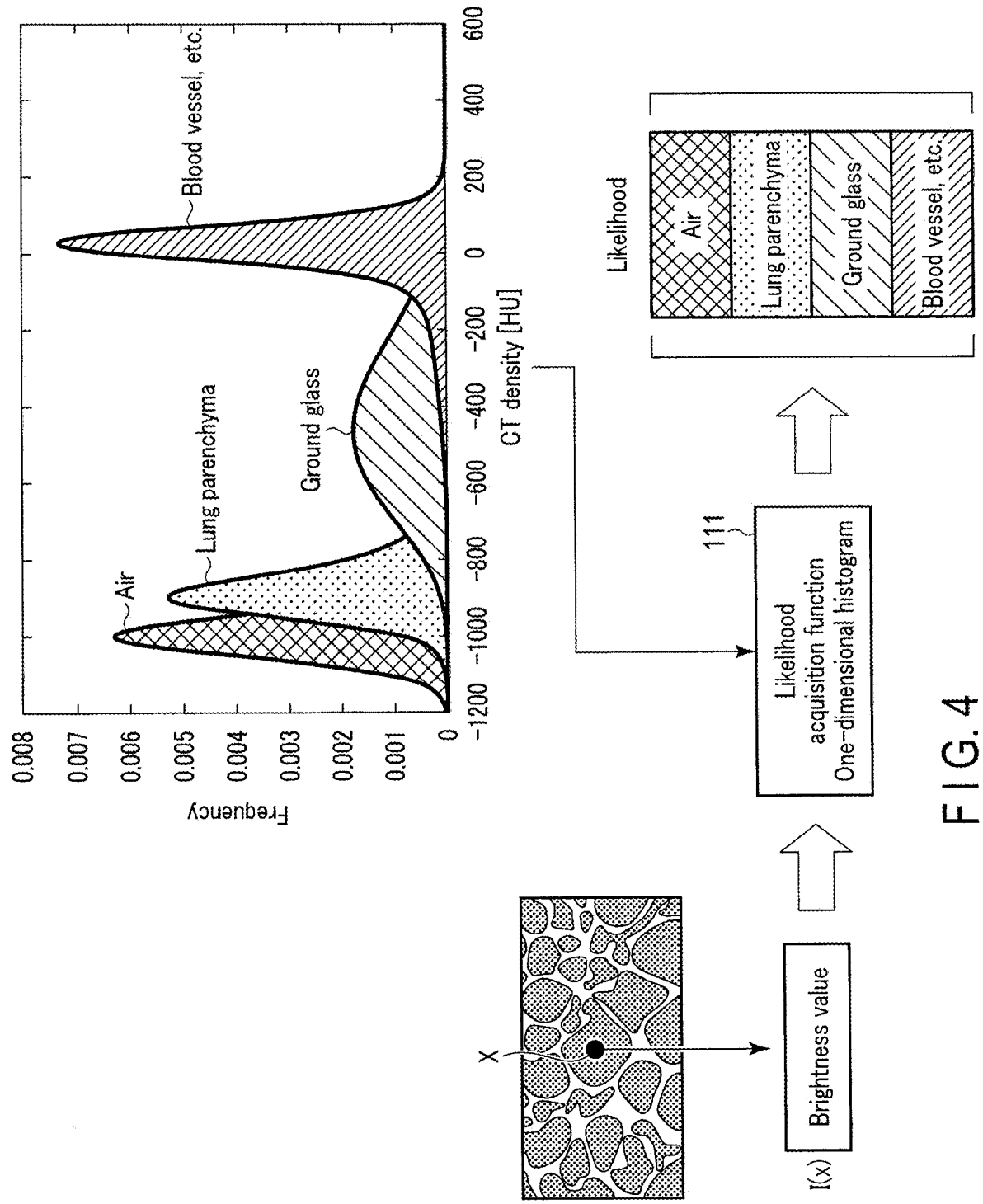
FIG. 4 is a diagram showing processing in which a likelihood value is acquired by a likelihood acquisition function shown in FIG. 2.

Specifically, for example, the processing circuitry 11 acquires likelihood values using one-dimensional histograms representing frequency distributions of the substances and structures in the body. FIG. 4 is a diagram schematically showing an example of processing in which likelihood values are acquired by the likelihood acquisition function 111 shown in FIG. 2. FIG. 4 explains an example of a case of calculating likelihood values regarding a CT image of a region of interest belonging to a lung field.

Pixel values of a CT image, with the air being −1000 HU and water being 0 HU as references, are distributed within a specific range in a histogram set for each of the substances and structures in the body. In particular, the air is often distributed within a range of −950 HU or less, a lung field (lung parenchyma) of −950 HU to −850 HU, a ground glass structure of −850 HU to −300 HU, and a blood vessel, etc. of −300 HU or more. Since a pixel value of a textual pattern also changes depending on the kind of disease, in which range a pixel value is distributed is an important characteristic in identification.

The memory 15 stores histograms as shown in FIG. 4 in advance. The processing circuitry 11 reads the histograms from the memory 15, and calculates four likelihood values from one pixel value based on the read histograms. Specifically, as the distribution of the four substances shown in FIG. 4 is respectively a probability density function $p(I(x)|c_k)$ (k=1: air, 2: lung parenchyma, 3: ground glass structure, 4: blood vessel, etc.), if a pixel value in a pixel position x is $I(x)$, a posterior probability can be calculated using Bayes theorem as follows.

[Equation 1]

$$p(c_k \mid I(x)) = \frac{p(I(x) \mid c_k)p(c_k)}{p(I(x))} = \frac{p(I(x) \mid c_k)p(c_k)}{\sum_{j=1}^{4} p(I(x) \mid c_j)p(c_j)} \quad (1)$$

where $p(c_k)$ represents a posterior probability, which may be uniform (=1/4). The processing circuitry 11 uses, as a likelihood value, a probability (0 to 1) that a pixel value belongs to each distribution, which is calculated by Equation (1). The processing circuitry 11, for example, performs the calculation indicated in Equation (1) for all the pixels included in the CT image data, and acquires a plurality of likelihood values for each pixel.

In addition, for example, the processing circuitry 11 may acquire a likelihood value using a two-dimensional co-occurrence histogram. The likelihood value of Equation (1) is calculated from one pixel value, and thus does not include spatial information. Accordingly, it may be difficult to represent a shape of a textual pattern. Thus, a co-occurrence histogram of a pixel value pair present in a spatially-close position may be used.

FIG. 5 is a diagram schematically showing an example of processing of acquiring likelihood values using co-occurrence histograms. FIG. 5 explains an example of a case of calculating likelihood values regarding a CT image of a region of interest belonging to a lung field. The memory 15 stores co-occurrence histograms as shown in FIG. 5 in advance. The processing circuitry 11 reads the co-occurrence histograms from the memory 15 in the likelihood acquisition function 111, and calculates a plurality of likelihood values from one pixel value based on the read co-occurrence histograms. Specifically, the processing circuitry 11, where a pixel value in a pixel position x is $I(x)$, and a pixel value in a position y apart from x for distance r is $I(y)$, obtains a concurrent probability density function $p(I(x), I(y)|c_k,r)$, (k=1: air, 2: lung parenchyma, 3: ground glass structure, 4: blood vessel, etc.). Then, the processing circuitry 11 calculates a posterior probability as shown in Equation (2), and uses the calculated posterior probability as a likelihood value.

[Equation 2]

$$p(c_k \mid I(x), I(y), r) = \frac{p(I(x), I(y) \mid c_k, r)p(c_k)}{p(I(x), I(y) \mid r)} = \frac{p(I(x), I(y) \mid c_k, r)p(c_k)}{\sum_{j=1}^{4} p(I(x), I(y) \mid c_j, r)p(c_j)} \quad (2)$$

Figure 6:
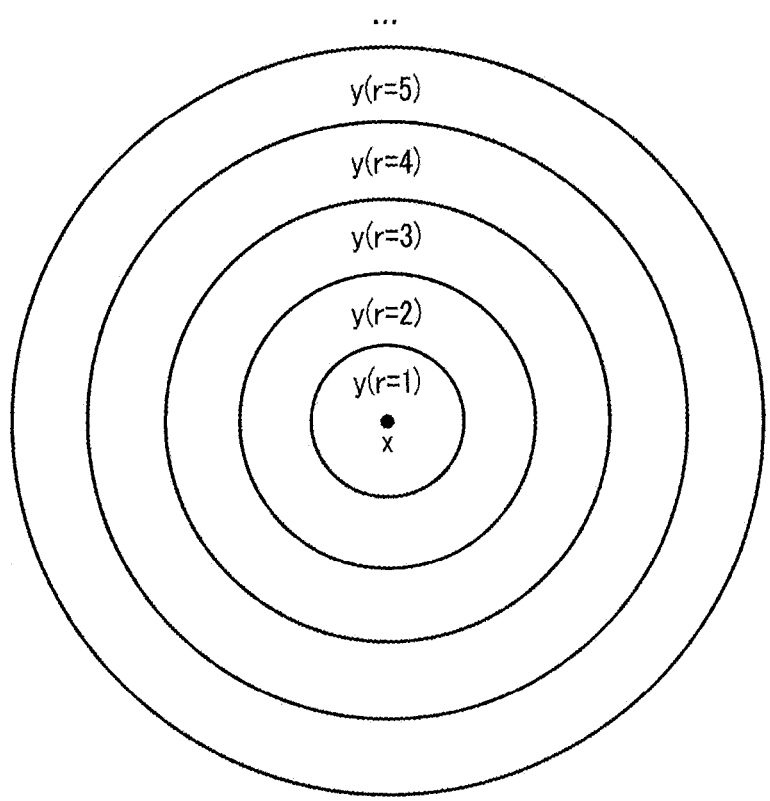
FIG. 6 is a diagram showing distances between pixel positions.

If r=0, x=y. Thus, the posterior probability obtained by Equation (2) is a value equal to the posterior probability obtained by Equation (1). Herein, a plurality of candidates can be considered as the pixel position y, but for example, as shown in FIG. 6, it is preferable to use an average value of a plurality of likelihood values acquired from points on a circumference at the same distance from x. FIG. 5 shows an example of a result calculated with r as a parameter (r=1 to 5). Four likelihood values can be acquired for each distance r, and if all five distances (r=1 to 5) are used, the number of likelihood values to be acquired is 20 (=4×5) in total. The processing circuitry 11, for example, performs the calculation shown in Equation (2) for all the pixels included in the CT image data, and acquires a plurality of likelihood values for each pixel.

Using a plurality of distances makes it possible to construe structures with different scales. In addition, it is possible to identify a shape of a textual pattern while taking spatial information into account. Note that the processing circuitry 11 can also extend the processing using two-dimensional co-occurrence histograms to processing using multi-dimensional co-occurrence histograms using three or more pixel values.

In addition, for example, the processing circuitry 11 may acquire a likelihood value using a decision tree model. FIG. 7 is a diagram schematically showing an example of processing of acquiring a likelihood value using a decision tree model. FIG. 7 explains an example of a case of calculating a likelihood value regarding a CT image of a region of interest belonging to a lung field. According to FIG. 7, the processing circuitry 11 determines a likelihood value based on a frequency distribution set in a terminal node of the decision tree model.

Specifically, as shown in FIG. 7, for example, a plurality (M models) of tree structures that branch based on a large/small relation of a pixel value difference of pixels at two random points in a local region of a predetermined width, have been created in advance. If, for example, four patterns of regions each representing air, lung parenchyma, ground glass, and blood vessels, are used as inputs, the likelihoods for air, lung parenchyma, ground glass, and blood vessels can be calculated based on frequency distributions of learning samples that have reached terminal nodes. Note that a plurality of widths are set for the local region, and a tree structure is created for each of the local regions of the set widths. Information relating to the tree structures are stored in the memory 15.

When a local region of a predetermined width is input in the likelihood acquisition function 111, the processing circuitry 11 selects a pixel pair at two random points in the region using the trained decision tree models. The processing circuitry 11 repeats branching based on the large/small relation of the pixels at the two points in the local region, and acquires the frequency distributions of the learning samples set in the terminal nodes. Based on the acquired frequency distributions, the processing circuitry 11, for example, calculates likelihood values for air, lung parenchyma, ground glass, and blood vessels. For example, the processing circuitry 11 may set average values of likelihood values for each of a plurality (M models) of decision trees as likelihood values for air, lung parenchyma, ground glass, and blood vessels.

The processing circuitry 11 acquires a plurality of likelihood values for all the pixels included in the CT image data while sliding the input predetermined local region. In addition, the processing circuitry 11 performs similar processing for a plurality of widths of local regions stored in the memory 15, and acquires a plurality of likelihood values for each stored local region.

Furthermore, for example, the processing circuitry n may acquire a likelihood value using an enhancing filter. FIG. 8 is a diagram schematically showing an example of processing of acquiring a likelihood value using an enhancing filter. FIG. 3 explains an example of a case of calculating a likelihood value regarding a CT image of a region of interest belonging to a lung field. In a lung, a cluster structure, such as a nodule, a tubular structure, such as a blood vessel, and a membrane structure, such as an interfoliaceous membrane, are included. Accordingly, acquiring likelihood values of the cluster, tubular, and membrane structures provides important information for identification of a textural pattern. According to FIG. 8, the processing circuitry 11 acquires likelihood values based on an enhancing filter for substances and structures in the body.

Note that the processing circuitry 11, for example, may have an identification function using the trained neural network, etc. for acquiring likelihood values for the structures. At this time, in the memory 15, for example, data relating to the trained neural network has been stored in advance. The processing circuitry 11, in the identification function, acquires the likelihood values for the structures using the trained neural network based on the data stored in the memory 15.

Note that in the explanations of the likelihood acquisition function 111 using FIGS. 4-8, an example is explained, in which the processing circuitry 11 acquires likelihood values for seven kinds of substances and structures of air, lung parenchyma, a ground glass opacity, a blood vessel, a cluster structure, a tubular structure, and a membrane structure from one pixel included in the CT image. However, the embodiment is not limited to this case. The processing circuitry 11 may acquire likelihood values for other substances and structures. For example, a solid shadow and a nodule may be included in the CT image. In addition, in the CT image, a linear structure, instead of the tubular structure, may be included, and further a plate structure, instead of the membrane structure, may be included. In a case where regions other than the lungs are included in the CT image, a gas, a fat tissue, water, a soft tissue, a calcified tissue, etc., that can be classified based on pixel values, may be included in the CT image. The processing circuitry 11 may acquire at least any one of likelihood values for air, lung parenchyma, a ground glass opacity, a solid shadow, a blood vessel, a nodule, a gas, a fat tissue, water, a soft tissue, a calcified tissue, a cluster structure, a tubular or linear structure, and a membrane or plate structure.

Figure 9:
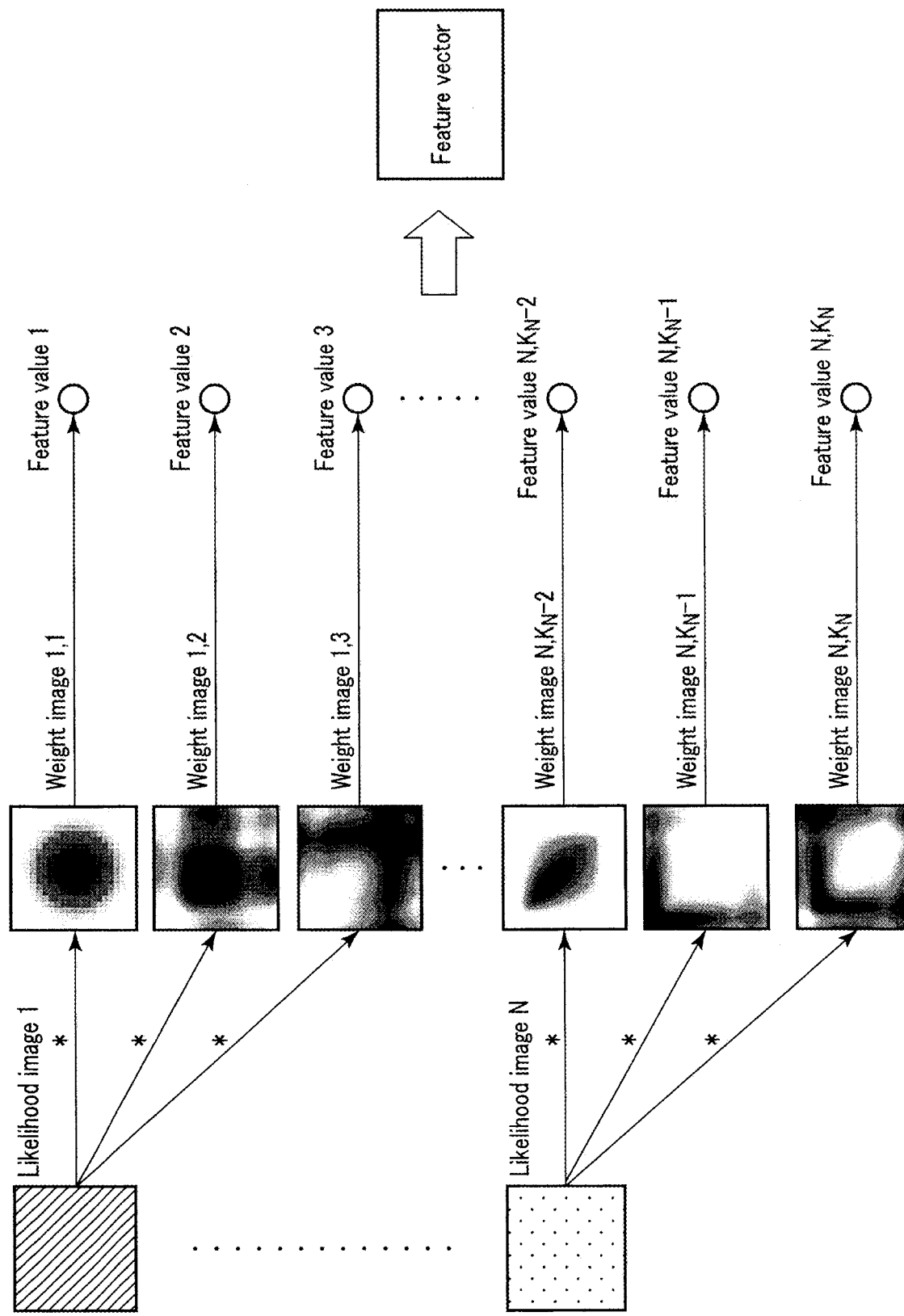
FIG. 9 is a diagram showing processing in which a feature vector is generated by a feature value calculation function shown in FIG. 2.

Next, processing of the feature value calculation function 112 shown in FIG. 2 will be specifically explained. The processing circuitry 11, for example, executes the feature value calculation function 112 when acquiring likelihood values for each pixel included in the CT image. FIG. 9 is a diagram schematically showing an example of processing in which a feature vector is generated by the feature value calculation function 112 shown in FIG. 2. In the feature value calculation function 112, the processing circuitry 11 multiplies N types of likelihood values acquired in each pixel of a CT image by the likelihood acquisition function 111 by an appropriate weighting factor. The processing circuitry 11 generates one feature vector by adding together the likelihood values multiplied by the weighting factor over the entire image.

Specifically, if a vector in which likelihood values of a channel i (i=1 to N) are arranged is a vector $v_i$, the processing circuitry 11 prepares $K_i$ pieces of vectors $w_i$, in which weighting factors of the same length as that of the vector $v_i$ are arranged. The processing circuitry 11 arranges $K_i$ pieces of vectors $w_i$ to be set as a matrix $W_i$ shown below.

[Equation 3]

$$W_i = [w_{i,1} \ldots w_{i,K_j}] \in \mathcal{R}^{V \times K}, \quad (3)$$

In Equation (3), V represents the number of pixels.

The processing circuitry 11 calculates a vector u with feature values arranged using the matrix $W_i$, as follows.

[Equation 4]

$$u = \begin{bmatrix} W_1^T v_1 \\ \vdots \\ W_N^T v_N \end{bmatrix} \in \mathcal{R}^P, \quad (4)$$

$$P = \sum_{i=1}^{N} K_i$$

In equation (4), P represents the total number of feature values. The processing circuitry 11 generates a feature vector by adding together the calculated vector u over the entire image.

Note that the processing circuitry 11 may calculate the vector u by adding a bias vector b, as follows.

[Equation 5]

$$u = \begin{bmatrix} W_1^T v_1 + b_1 \\ \vdots \\ W_N^T v_N + b_N \end{bmatrix} \in \mathcal{R}^P \quad (5)$$

In addition, in the explanations using Equations (3) to (5), a weighting factor is set for each channel. However, the embodiment is not limited to the above case. An identical weighting factor may be used.

Figure 10:
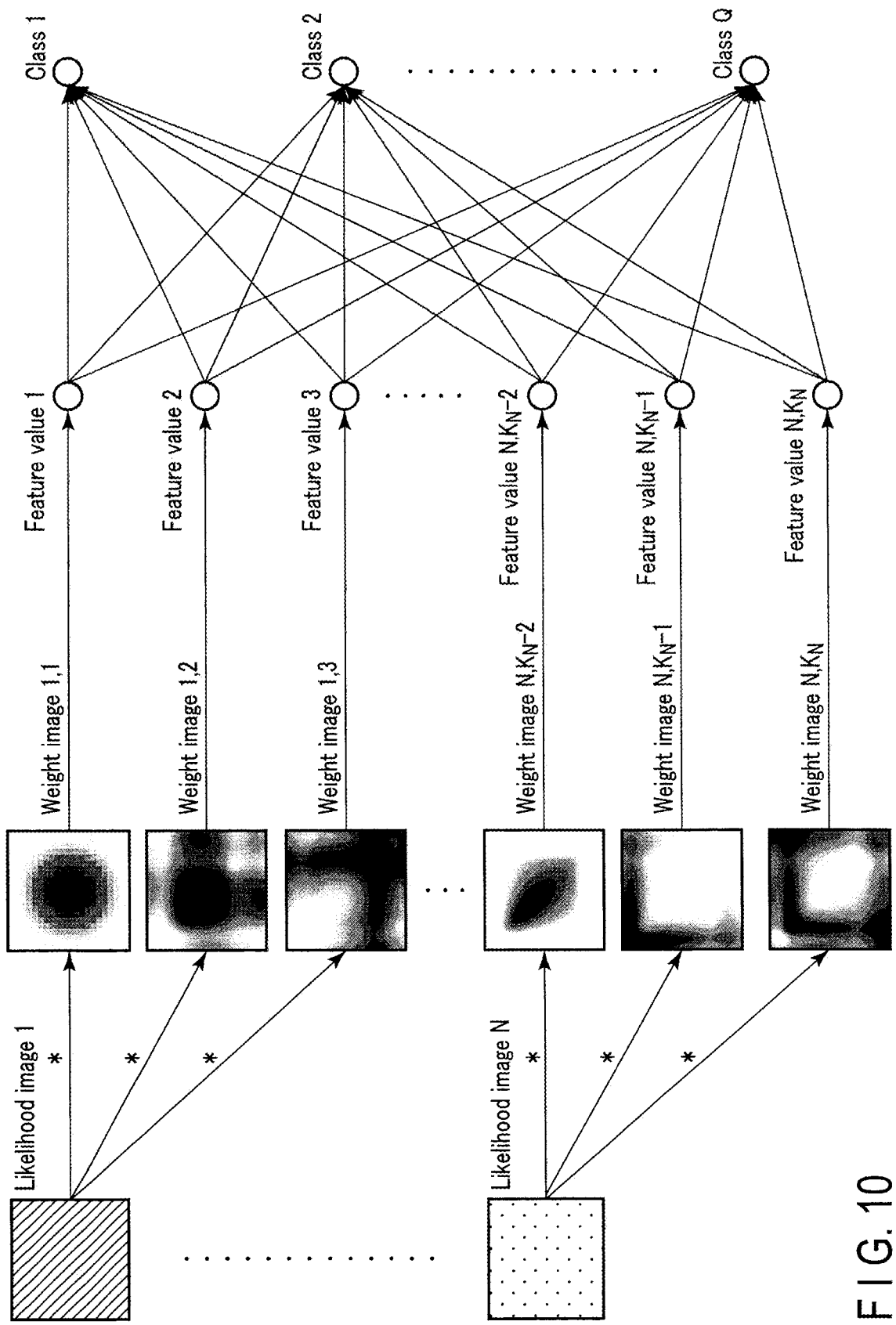
FIG. 10 is a diagram showing a training process using a neural network.

A weighting factor to be multiplied to a likelihood value is determined by various techniques. For example, as a weighting factor, a determined value, such as a Gaussian filter, a Gabor filter, an average value filter, and a box filter, may be used. In addition, as a weighting factor, an optimal value may be determined by machine learning. FIG. 10 is a diagram schematically showing an example of training process using a neural network. For example, a network is prepared, which connects, at all coupling layers, output units having been matched in advance with the number of textual patterns to be identified, and feature values acquired by being multiplied by a weighting factor. Note that an initial value of the weighting factor is preferably set randomly from Gaussian distribution, uniform distribution, etc. For example, the weighting factor is repeatedly updated using an error inverse propagation method. In the case of using the machine learning, a weighting factor is automatically determined in line with a problem to be identified. Thereby, identification accuracy may be improved more than using a weighting factor determined in advance, such as a Gaussian filter.

In the above manner, in the present embodiment, the processing circuitry 11 acquires desired medical image data by the image acquisition function 110. The processing circuitry 11 acquires spatial distribution of likelihood values regarding a plurality of kinds of substances and structures in a body for each textual pattern based on the medical image data by the likelihood acquisition function 111. By the feature value calculation function 112, the processing circuitry 11 calculates feature values in a predetermined region of the medical image based on the acquired spatial distribution. In this way, the processing circuitry 11 does not extract features directly from an image, but performs feature extraction using likelihoods of substances and structures in a body, which are associated with a textual pattern to be identified. Thereby, the processing circuitry 11 can obtain feature values with high identification capability.

Thus, according to the image processing apparatus 10 of the present embodiment, identification accuracy of a textual pattern of a medical image can be improved.

Figure 11:
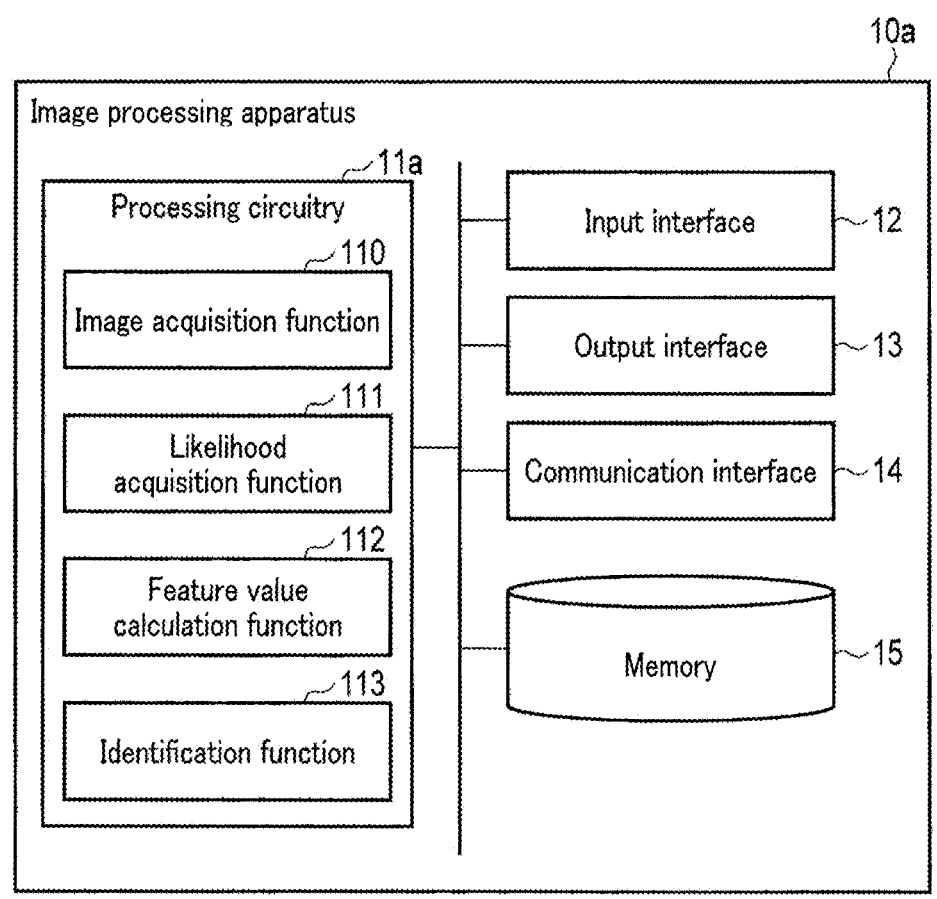
FIG. 11 is a diagram showing an example of a case where processing circuitry of the image processing apparatus shown in FIG. 1 has an identification function.

Described in the above embodiment is a case where the processing circuitry 11 has the image acquisition function 110, the likelihood acquisition function 111, and the feature value calculation function 112. However, the embodiment is not limited to the above case. For example, as shown in FIG. 11, the processing circuitry 11a may have an identification function 113. The processing circuitry 11a has, by executing a program stored in the memory 13, the image acquisition function 110, the likelihood acquisition function 111, the feature value calculation function 112, and the identification function 113.

Figure 12:
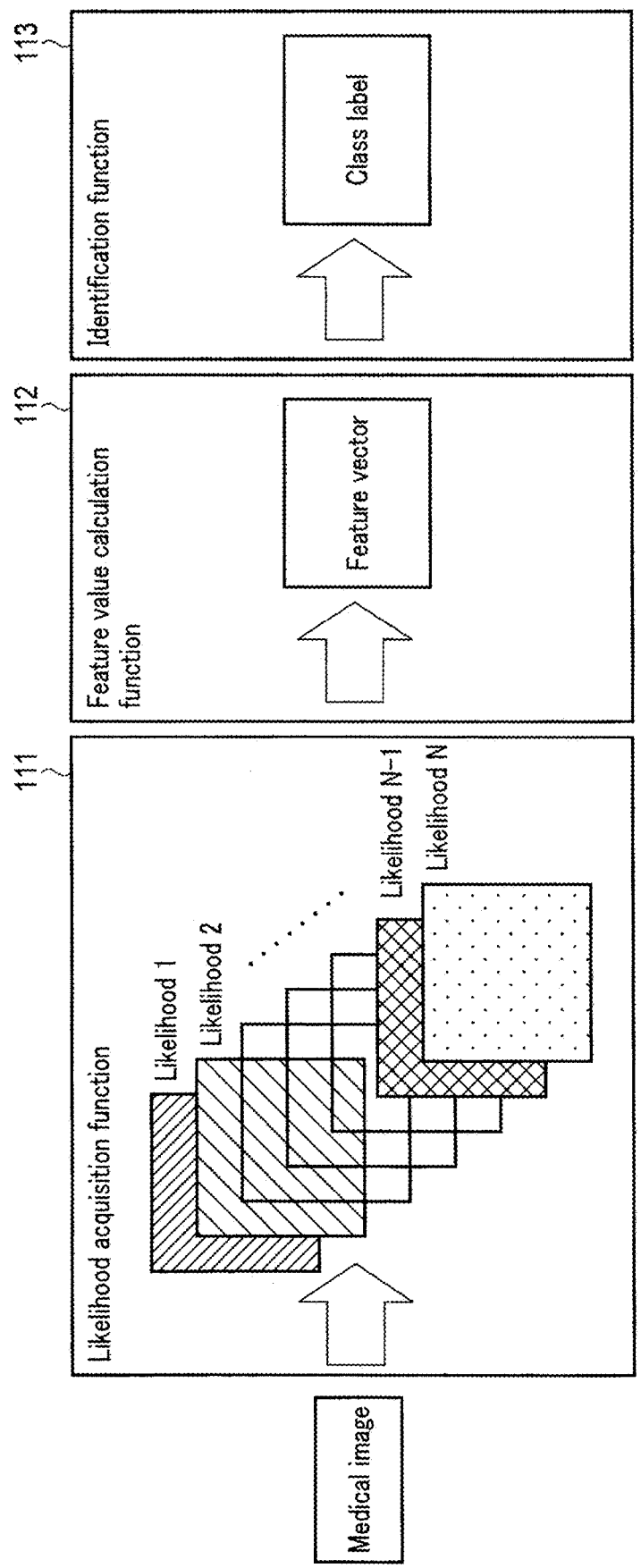
FIG. 12 is a diagram explaining another example of an operation of the processing circuitry shown in FIG. 2.

The identification function 113 identifies a textual pattern, such as a preset lesion, body tissue, or organ using a model of machine learning trained with feature vectors acquired by the feature value calculation function 112. At this time, for example, in the memory 15, data relating to the trained model for identifying a predetermined textual pattern is stored in advance. The number of patterns to be identified by the identification function 113 is discretionary, and may be larger or smaller than the number of types of acquired likelihood values. The number of patterns to be identified is, for example, two in a case of identifying benignancy and malignancy. FIG. 12 is a diagram for schematically explaining an operation of the processing circuitry 11a shown in FIG. 11. According to FIG. 12, the processing circuitry 11a acquires likelihood values for each pixel of a medical image to generate likelihood images of likelihood 1 to likelihood N. The processing circuitry 11a generates a feature vector based on the likelihood images of likelihood 1 to likelihood N. The processing circuitry 11a then identifies a textual pattern, such as a preset lesion, body tissue, or organ using the trained model of machine learning trained with feature vectors acquired as a sample, based on the generated feature vector.

As an algorithm of machine learning used in the identification function 113, discrimination analysis, logistic regression, a support vector machine, a neural network, Randomized Trees, and a subspace method, etc. can be utilized. Note that by combining any one of these, and conditional random fields and graph cuts, a textual pattern may be identified by taking neighboring relationship of pixels into consideration.

Figure 13:
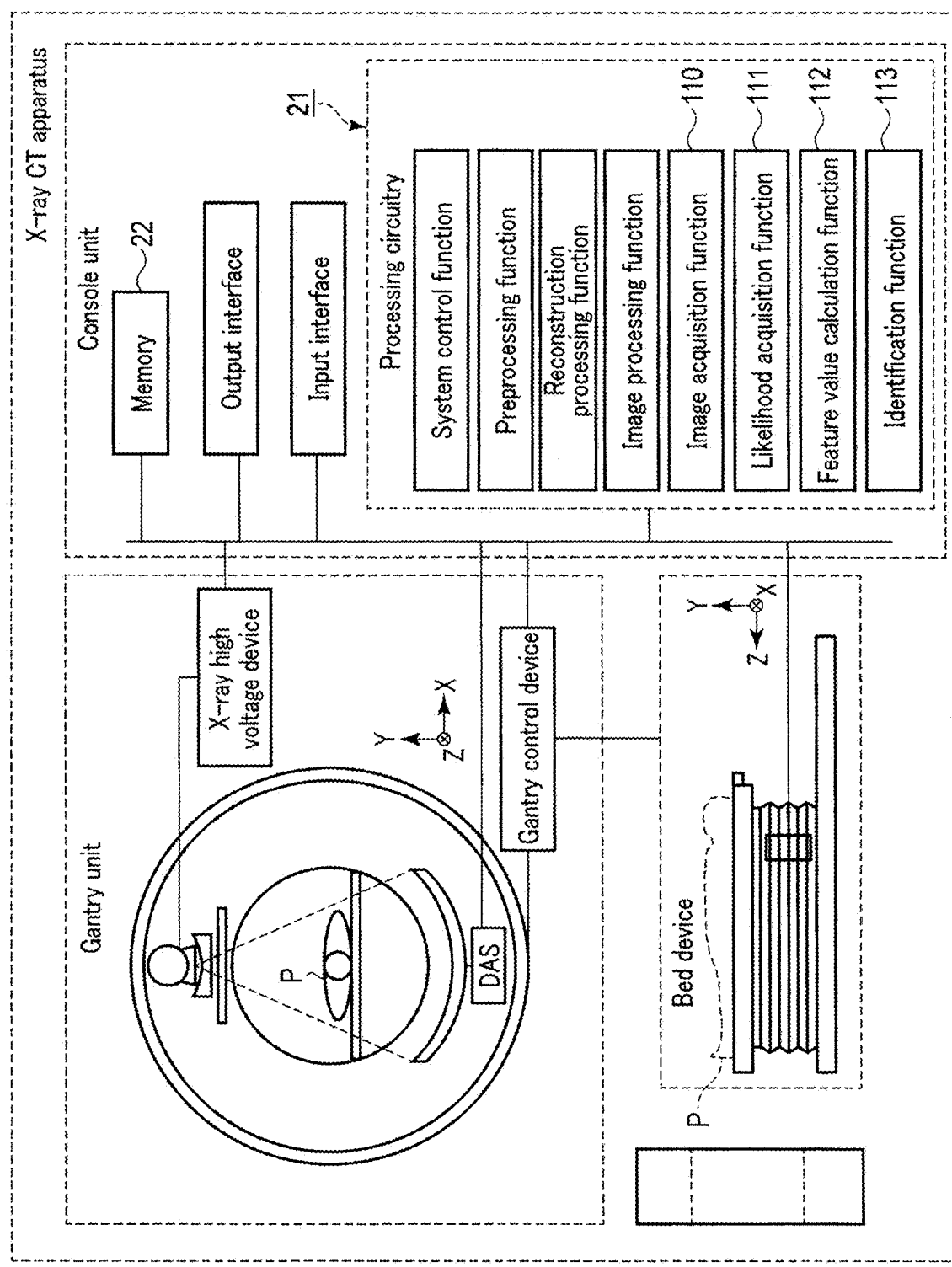
FIG. 13 is a diagram showing a functional configuration of the medical image diagnostic apparatus shown in FIG. 1.

Described in the present embodiment is a case where the image acquisition function 110, the likelihood acquisition function 111, the feature value calculation function 112, and the identification function 113 are provided in the image processing apparatus 10. However, the embodiment is not limited to the above case. The image acquisition function 110, the likelihood acquisition function 111, the feature value calculation function 112, and the identification function 113 may be provided in the medical image diagnostic apparatus 20. FIG. 13 is a diagram showing an example of a functional configuration of an X-ray CT apparatus in a case where an X-ray CT apparatus, which is an example of the medical image diagnostic apparatus 20, has the image acquisition function lie, the likelihood acquisition function ill, the feature value calculation function 112, and the identification function 113. According to FIG. 13, processing circuitry 21 of the medical image diagnostic apparatus 20, by executing a program stored in a memory 22, realizes the image acquisition function 110, the likelihood acquisition function 111, the feature value calculation function 112, and the identification function 113. Note that the processing circuitry 21 may perform the likelihood acquisition function 111 for CT image data generated by image reconstruction processing. In this case, the processing circuitry 21 does not necessarily need to perform the image acquisition function 110.

The image acquisition function 110, the likelihood acquisition function 111, the feature value calculation function 112, and the identification function 113 according to the present embodiment can be realized by, for example, using a generic computer device as basic hardware. Namely, the image processing apparatus 10 and the medical image diagnostic apparatus 20 can realize the image acquisition function 110, the likelihood acquisition function 111, the feature value calculation function 112, and the identification function 113 by causing a processor mounted in a computer device to execute a program. At this time, the image processing apparatus 10 and the medical image diagnostic apparatus 20 may realize the image acquisition function 110, the likelihood acquisition function 111, the feature value calculation function 112, and the identification function 113 by installing the above program in advance, in addition, the image processing apparatus 10 and the medical image diagnostic apparatus 20 may realize the image acquisition function 110, the likelihood acquisition function 111, the feature value calculation function 112, and the identification function 113 by reading the above program from a storage medium, such as a CD-ROM, or receiving the above program via a network and appropriately installing the program. Positional information to specify a three-dimensional CT image input to the image processing apparatus 10 and a structure of an extraction target may be stored in a storage medium, etc., such as a memory, a hard disk, or CD-R, CD-RW, DVD-RAM, and DVD-R, which is incorporated into or externally attached to the above computer device.

A CT image is raised as an example of a medical image in the above embodiment. However, the medical image is not limited to a CT image. The medical image may be other images, such as an MR image acquired by an MRI apparatus. The processing circuitry 11, for example, acquires likelihood values based on structures included in an MR image. Then, the processing circuitry 11 calculates feature values by multiplying the acquired likelihood values by a weighting factor to acquire a feature vector.

The term "processor" used in the above explanation means, for example, circuitry such as a Central Processing unit (CPU), a Graphics Processing Unit (GPU), an Application Specific Integrated Circuit (ASIC), or a programmable logic device (for example, a Simple Programmable Logic Device (SFLD), a Complex Programmable Logic Device (CPLD), or a Field Programmable Gate Array (FPGA)). The processor realizes its function by reading and executing a program stored in the memory 15. Instead of storing a program on the memory 15, the program may be directly integrated into the circuitry of the processor. In this case, the function is realized by reading and executing the program integrated into the circuitry. Bach processor of the above embodiment is not limited to a case where each processor is configured as a single circuit; a plurality of independent circuits may be combined into one processor to realize the function of the processor.

The image acquisition function 110, the likelihood acquisition function 111, the feature value calculation function 112, and the identification function 113 in the present embodiment may be realized by a respectively corresponding image acquisition unit, likelihood acquisition unit, feature value calculation unit, and identification unit. The operation of the constituent elements explained as "units" in the present embodiment may be realized by hardware, software, or a combination thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An image processing apparatus comprising processing circuitry configured to:
   acquire medical image data;
   based on a pixel value of the medical image data, obtain spatial distribution of likelihood values representing a likelihood corresponding to a textual pattern included in the medical image data based on each of a plurality of textual patterns;
   calculate a feature value based on a likelihood value of each of the plurality of textual patterns; and
   identify a kind of lesion, body tissue, or organ included in the medical image based on the feature value,
   wherein the processing circuitry acquires the likelihood values according to pixel values of each pixel and pixels that surround the each pixel.

2. The image processing apparatus according to claim 1, wherein the processing circuitry sets a plurality of distances between the each pixel and the pixels that surround the each pixel, and acquires the likelihood values according to the pixel values of the each pixel and the pixels that surround the each pixel for each of the distances.

3. The image processing apparatus according to claim 1, wherein the processing circuitry calculates the feature values for each of the plurality of textual patterns by multiplying the likelihood values for the respective textual pattern by preset weighting factors.

4. The image processing apparatus according to claim 1, wherein the processing circuitry acquires the likelihood values based on frequency distributions of substances and structures in a body, which correspond to the pixel value.

5. The image processing apparatus according to claim 4, wherein the frequency distributions include a one-dimensional histogram or a multi-dimensional co-occurrence histogram.

6. The image processing apparatus according to claim 1, wherein the medical image includes a CT image.

7. The image processing apparatus according to claim 6, wherein the textual pattern includes a pattern of a substance in a body, the substance being at least any one of air, a gas, a fat tissue, water, a soft tissue, and a calcified tissue, which can be classified based on a pixel value of the CT image.

8. The image processing apparatus according to claim 6, wherein the medical image includes an image of a lung.

9. The image processing apparatus according to claim 8, wherein the textual pattern includes a pattern of a substance in a body, the substance being at least any one of air, lung parenchyma, a ground glass opacity, a solid shadow, a blood vessel, and a nodule.

10. The image processing apparatus according to claim 1, wherein the textual pattern includes a pattern of a structure in a body, the structure being at least any one of a cluster structure, a tubular or linear structure, and a plate or membrane structure of a body tissue.

11. The image processing apparatus according to claim 1, wherein the processing circuitry is further configured to calculate the likelihood value based on a co-occurrence histogram.

12. The image processing apparatus according to claim 1, wherein the processing circuitry is further configured to calculate the likelihood value using a decision tree model.

13. The image processing apparatus according to claim 1, wherein the processing circuitry is further configured to acquire the likelihood value based on a trained neural network.

14. The image processing apparatus according to claim 1, wherein the processing circuitry is further configured to calculate the feature value based on a network which connects, at all coupling layers, output units having been matched in advance with a number of textual patterns to be identified, and feature values acquired by being multiplied by a weighting factor.

15. The image processing apparatus according to claim 1 wherein the processing circuitry is further configured to identify the kind of lesion, the body tissue, or the organ included in the medical image using a machine learning algorithm, the machine learning algorithm being at least one of discrimination analysis, logistic regression, a support vector machine, a neural network, Randomized Trees, or a subspace method.

16. The image processing apparatus according to claim 1, wherein the processing circuitry is further configured to identify the kind of lesion, the body tissue, or the organ included in the medical image using a machine learning algorithm, the machine learning algorithm being a combination of any one of discrimination analysis, logistic regression, a support vector machine, a neural network, Randomized Trees, a subspace method, and a conditional random field or a graph cut.

* * * * *